(12) United States Patent
Weiser et al.

(10) Patent No.: US 8,771,904 B2
(45) Date of Patent: *Jul. 8, 2014

(54) METHOD FOR PRODUCING HOLOGRAPHIC MEDIA

(75) Inventors: Marc-Stephan Weiser, Leverkusen (DE); Thomas Rölle, Leverkusen (DE); Dennis Hönel, Zülpich (DE); Friedrich-Karl Bruder, Krefeld (DE); Thomas Fäcke, Leverkusen (DE)

(73) Assignee: Bayer MaterialScience AG (DE)

( * ) Notice: Subject to any disclaimer, the term of this patent is extended or adjusted under 35 U.S.C. 154(b) by 180 days.

This patent is subject to a terminal disclaimer.

(21) Appl. No.: 13/505,154

(22) PCT Filed: Nov. 2, 2010

(86) PCT No.: PCT/EP2010/066589
§ 371 (c)(1),
(2), (4) Date: Apr. 30, 2012

(87) PCT Pub. No.: WO2011/054793
PCT Pub. Date: May 12, 2011

(65) Prior Publication Data
US 2012/0214090 A1 Aug. 23, 2012

(30) Foreign Application Priority Data
Nov. 3, 2009 (EP) .................................. 09013765

(51) Int. Cl.
*G03H 1/02* (2006.01)
*G01N 5/04* (2006.01)
*G03H 1/04* (2006.01)

(52) U.S. Cl.
CPC ............. *G03H 1/04* (2013.01); *G03H 2227/04* (2013.01); *G03H 2260/12* (2013.01); *G03H 2260/54* (2013.01); *G01N 5/04* (2013.01)
USPC .......................... 430/1; 430/2; 359/3; 374/14

(58) Field of Classification Search
None
See application file for complete search history.

(56) References Cited

U.S. PATENT DOCUMENTS

| 5,679,710 A * | 10/1997 | Davy et al. .................... 514/547 |
| 2003/0087104 A1* | 5/2003 | Dhar et al. .................. 428/422.8 |

(Continued)

FOREIGN PATENT DOCUMENTS

| EP | 134861 | * | 3/1985 |
| EP | 684222 | * | 11/1995 |

(Continued)

OTHER PUBLICATIONS

International Search Report for PCT/EP2010/066589 mailed Jan. 17, 2011.

*Primary Examiner* — Martin Angebranndt
(74) *Attorney, Agent, or Firm* — Drinker Biddle & Reath LLP (57) ABSTRACT

The invention relates to a method for producing holographic media, wherein a photopolymer formulation comprising matrix polymers, writing monomers, a photoinitiator system, and optionally auxiliary materials and additives as components is provided, the photopolymer formulation is applied as a coating on the surface of a carrier film and the photopolymer formulation is dried on the carrier film at a temperature XX<T>YY DEG C, wherein only those compounds having TGA 95 values >100 DEG C. and at least 30 DEG C. above the temperature T are selected as components for the photopolymer formulation. The invention further relates to a holographic medium that can be obtained by means of the method according to the invention.

15 Claims, 2 Drawing Sheets

(56) References Cited

U.S. PATENT DOCUMENTS

| | | | |
|---|---|---|---|
| 2005/0185232 A1* | 8/2005 | Teranishi et al. | 359/3 |
| 2006/0166104 A1* | 7/2006 | Setthachayanon et al. | 430/1 |
| 2008/0254374 A1* | 10/2008 | Yamada et al. | 430/2 |
| 2008/0311483 A1* | 12/2008 | Stockel et al. | 430/2 |
| 2008/0312403 A1* | 12/2008 | Stockel et al. | 528/59 |
| 2009/0062419 A1* | 3/2009 | Stockel et al. | 522/109 |
| 2009/0087753 A1* | 4/2009 | Satou et al. | 430/2 |
| 2009/0185470 A1* | 7/2009 | Stoeckel et al. | 369/103 |
| 2010/0020373 A1* | 1/2010 | Askham | 359/3 |
| 2010/0036013 A1* | 2/2010 | Roelle et al. | 522/174 |
| 2010/0086860 A1* | 4/2010 | Roelle et al. | 430/2 |
| 2010/0086861 A1* | 4/2010 | Weiser et al. | 430/2 |
| 2010/0087564 A1* | 4/2010 | Weiser et al. | 522/95 |
| 2010/0112459 A1* | 5/2010 | Weiser et al. | 430/2 |
| 2010/0203241 A1* | 8/2010 | Weiser et al. | 427/162 |
| 2011/0065827 A1* | 3/2011 | Facke et al. | 522/173 |
| 2011/0189591 A1* | 8/2011 | Weiser et al. | 430/2 |
| 2011/0236803 A1* | 9/2011 | Weiser et al. | 430/2 |
| 2011/0311905 A1* | 12/2011 | Honel et al. | 430/2 |
| 2012/0214089 A1* | 8/2012 | Honel et al. | 430/2 |
| 2012/0214895 A1* | 8/2012 | Rolle et al. | 522/78 |
| 2012/0219883 A1* | 8/2012 | Bruder et al. | 430/2 |
| 2012/0219884 A1* | 8/2012 | Weiser et al. | 430/2 |
| 2012/0219885 A1* | 8/2012 | Facke et al. | 430/2 |
| 2012/0231376 A1* | 9/2012 | Rolle et al. | 430/2 |
| 2012/0231377 A1* | 9/2012 | Weiser et al. | 430/2 |
| 2012/0237856 A1* | 9/2012 | Rolle et al. | 430/2 |
| 2012/0302659 A1* | 11/2012 | Rolle et al. | 522/173 |
| 2012/0321997 A1* | 12/2012 | Rolle et al. | 430/2 |
| 2012/0321998 A1* | 12/2012 | Rolle et al. | 430/2 |
| 2013/0177746 A1* | 7/2013 | Facke et al. | 428/195.1 |
| 2013/0224634 A1* | 8/2013 | Berneth et al. | 430/2 |
| 2013/0252140 A1* | 9/2013 | Facke et al. | 430/2 |

FOREIGN PATENT DOCUMENTS

| | | |
|---|---|---|
| EP | 0700949 A2 | 3/1996 |
| EP | 09001952.2 | 2/2009 |
| EP | 09002180.9 | 2/2009 |
| EP | 09009651.2 | 7/2009 |
| EP | 2154129 A1 | 2/2010 |
| EP | 2219075 A1 | 8/2010 |
| EP | 2396358 A1 | 12/2011 |
| WO | WO-03/014178 A1 | 2/2003 |
| WO | WO-2008/125199 A1 | 10/2008 |

* cited by examiner

METHOD FOR PRODUCING HOLOGRAPHIC MEDIA

CROSS-REFERENCE TO RELATED APPLICATIONS

This application is a national stage application (under 35 U.S.C. §371) of PCT/EP2010/066589, filed Nov. 3, 2010, which claims benefit of European application 09013765.4, filed Nov. 3, 2009, both of which are incorporated herein by reference in their entirety for all their useful purposes.

BACKGROUND

The invention relates to a process for producing holographic media and to holographic media obtainable by the process.

Holographic media can be produced, for example, with the aid of special photopolymer formulations. Thus, for example, WO 2008/125199 A1 describes a photopolymer formulation which contains polyurethane-based matrix polymers, an acrylate-based writing monomer and photoinitiators. If the photopolymer formulation is cured, the writing monomer and the photoinitiators are embedded with an isotropic distribution in space in the resulting polyurethane matrix. In this way, a medium into which holograms can be incorporated by exposure to light is obtained.

This can be effected by means of the superposition of two coherent light sources, a three-dimensional structure which in general can be described by a regional change in the refractive index (refractive index modulation $\Delta n$) forming in the medium. Such structures are referred to as holograms, which can also be described as diffractive optical elements. The optical functions which are performed by such a hologram depend on the specific exposure to light.

For the uses of photopolymer formulations, the refractive index modulation $\Delta n$ produced by the holographic exposure to light in the photopolymer plays the decisive role. During the holographic exposure to light, the interference field of signal and reference light beam (in the simplest case, that of two plane waves is formed by the local photopolymerization of, for example, highly refractive acrylates at sites of high intensity in the interference field in a refractive index grating. The refractive index grating in the photopolymer (the hologram) contains all information of the signal light beam. By exposing the hologram only to the reference light beam, the signal can then be reconstructed. The strength of the signal reconstructed in this manner in relation to the strength of the incident reference light is referred to as diffraction efficiency or DE below. In the simplest case of a hologram which forms from the superposition of two plane waves, the DE is obtained from the quotient of the intensity of the light diffracted in the reconstruction and the sum of the intensities of incident reference light and diffracted light. The higher the DE, the more efficient is a hologram with respect to the quantity of reference light which is required in order to make the signal visible with a fixed brightness.

Highly refractive acrylates are capable of producing refractive index gratings having a high amplitude between regions with low refractive index and regions with high refractive index and hence permitting holograms with high DE and high $\Delta n$ in photopolymer formulations. It should be noted that DE is dependent on the product of $\Delta n$ and the photopolymer layer thickness d. The greater the product, the greater the possible DE (for reflection holograms). The width of the angular range in which the hologram becomes visible (reconstructed), for example in the case of exposure to monochromatic light, depends only on the layer thickness d. In the case of exposure of the hologram to, for example, white light, the width of the spectral region which can contribute to the reconstruction of the hologram likewise depends only on the layer thickness d. The smaller d, the greater are the respective acceptance widths.

If it is intended to produce bright and readily visible holograms, a high $\Delta n$ and small thickness d should be strived for, in particular so that DE is as large as possible. This means that the higher $\Delta n$, the more latitude achieved for establishing the layer thickness d for bright holograms without loss of DE. The optimization of $\Delta n$ in the optimization of photopolymer formulations is therefore of outstanding importance (P. Hariharan, Optical Holography, 2nd Edition, Cambridge University Press, 1996).

Attempts have therefore been made to date to realize as high a $\Delta n$ as possible by changing the composition of the photopolymer formulations used for the production of the holographic media. However, it has been found that the photopolymer formulations developed in laboratory experiments cannot be used without considerable problems in some cases for the industrial production of holographic media.

Such an industrial production process is described, for example, in European Patent Application not laid open as yet and having the application number 09001952.2. In this process, a photopolymer formulation is applied to a substrate material and then dried at elevated temperature. In this way, holographic media in the form of films can be obtained.

If the photopolymer formulations optimized in laboratory experiments for a high $\Delta n$ are used in the process described above, media are obtained in many cases which, in comparison with media which were produced on the laboratory scale, surprisingly had substantially lower $\Delta n$ values when holograms were recorded in them. It has therefore not been directly possible to date to use laboratory formulations for industrial production of holographic media.

Owing to an observed loss of mass in the production of holographic media, it is obviously presumed that, during the production, evaporation of individual components might occur especially in the area of drying. Taking into account the boiling points and the vapour pressures of the components used, however, it was not to be expected that, at the respective drying temperatures, these should be a cause of the observed loss of mass and hence a reason for the substantially lower $\Delta n$ values.

However, the vapour pressure is a parameter with the aid of which the suitability of components for use in the industrial production of holographic media cannot be tested. This is because the vapour pressure of a chemical compound is a physical constant which describes how a pure substance or a mixture of substances is in thermodynamic equilibrium with its liquid or solid phase. For dynamic systems, however, the vapour pressure gives no guidance.

Thus, the vapour pressure does not describe the situation which prevails, for example, in a continuously operated coating unit. Here, the photopolymer formulation applied with a small layer thickness extensively to a substrate film is dried by air circulation. The air circulation ensures that the gaseous phase is constantly removed. A thermodynamic equilibrium is therefore not established under these conditions.

It was therefore an object of the present invention to provide a (industrial) process with the aid of which it is possible to produce holographic media having a high $\Delta n$ value.

BRIEF DESCRIPTION OF EMBODIMENTS

This object is achieved by a process for producing holographic media in which i) a photopolymer formulation comprising, as components,
   A) matrix polymers
   B) writing monomers
   C) photoinitiator system
   D) optionally a non-photopolymerizable component
   E) and optionally catalysts, free radical stabilizers, solvents, additives and other auxiliaries and/or additives
is provided,
ii) the photopolymer formulation is applied extensively as a layer to a substrate film and
iii) the photopolymer formulation is dried on the substrate film at a temperature of 60<T<120° C., characterized in that only compounds whose TGA 95 values are >100° C. and are at least 30° C. above the temperature T are chosen as components for the photopolymer formulation.

In the case of a certain component present in a photopolymer formulation, the vapour pressure thereof is therefore not decisive for testing whether, during a drying process on open surfaces, there is a risk of said component evaporating from the formulation. Rather, the volatility of this chemical component should be determined, the TGA 95 value being taken as a measure here.

The TGA 95 value of a component is understood in the context of the present invention as being the temperature at which, for the respective component, a loss of mass of 5% by weight, based on the originally weighted amount of the component, has occurred. The TGA 95 value of the respective component can be measured by a thermogravimetric analysis, in which this temperature is determined.

BRIEF DESCRIPTION OF THE DRAWINGS

The foregoing brief description, as well as the following detailed description, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF EMBODIMENTS

Figure 1:
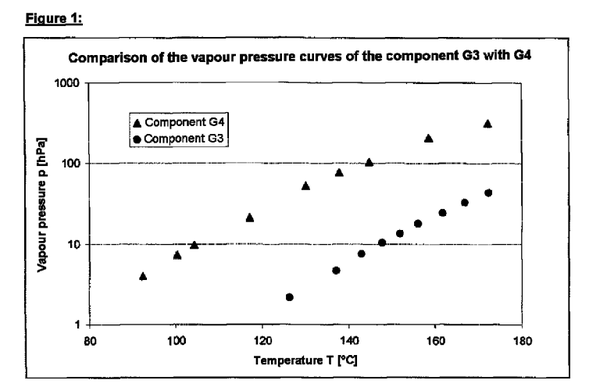
FIG. 1 illustrates a graph showing vapour pressure curves in the temperature range from 90 to 180° C.

The suitability of the TGA 95 values as a selection criterion is also demonstrated by the following experimental findings: for two components used for the production of holographic media, namely the component D2 (2,2,3,3,4,4,5,5,6,6,7,7,8,8,9,9-hexadecafluorononyl butylcarbamate) and component D3 (2,2,2-trifluoroethyl hexylcarbamate), the vapour pressures were determined under a nitrogen atmosphere in a circulation apparatus (isobarically in an ebulliometer) according to Röck in accordance with the OECD guideline for testing of chemicals, No. 104. The resulting vapour pressure curves are shown in FIG. 1 in the temperature range from 90 to 180° C. The resulting parameters of the Antoine equation $$lg \frac{P^{Sat}}{hPa} = A - \frac{B}{C + T(° C.)}$$

are accordingly:

TABLE 01

Physical data of the components D2 and D3

| Example | Parameters of the Antoine equation | | | Vapour pressure at 80° C. [hPa] | Vapour pressure at 100° C. [hPa] | TGA 95 [° C.] |
| --- | --- | --- | --- | --- | --- | --- |
| | A | B | C | | | |
| D2 | 6.5466 | 1053.404 | 42.458 | 0.13 | 0.42 | 111.8 |
| D3 | 15.6189 | 2616.075 | 90.3596 | 1.30 | 7.30 | 72.5 |

This shows that the equilibrium vapour pressure for a temperature of, for example, 100° C. is <10 hPa for both components D2 and D3, so that it would have been expected that the two components in the formulation would have sufficient stability. However, this is not the case. The TGA 95 values for the two components D2 and D3 correlate on the other hand substantially better with the observed behaviour and show that the two compounds are not suitable for the production of holographic media in a process according to the invention.

The TGA 95 values of the individual components can be determined in particular by weighing an amount of the sample of the respective component of about 10 mg into an aluminium pan having a volume of 70 μl, introducing the aluminium pan into an oven of a thermobalance, preferably of a TG50 thermobalance from Mettler-Toledo and measuring the loss of mass of the sample in the open aluminium pan at a constant oven heating rate of 20 K/min, the start temperature being 30° C. and the end temperature of the oven being 600° C., flushing the oven with a 200 ml/min nitrogen stream during the determination and determining, as the TGA 95 value of the respective component, the temperature at which a loss of mass of the sample of 5% by weight, based on the originally weighted amount of the sample, has occurred.

Preferably, the photopolymer formulation can be dried at a temperature of 70<T<100° C.

The matrix polymers used can preferably be polyurethanes, which are obtainable in particular by reacting an isocyanate component a) with an isocyanate-reactive component b).

The isocyanate component a) preferably comprises polyisocyanates. Polyisocyanates which may be used are all compounds known per se to a person skilled in the art or mixtures thereof, which have on average two or more NCO functions per molecule. These may have an aromatic, araliphatic, aliphatic or cycloaliphatic basis. Monoisocyanates and/or polyisocyanates containing unsaturated groups may also be concomitantly used in minor amounts.

For example, butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methane and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate and/or triphenylmethane 4,4',4"-triisocyanate are suitable.

Use of derivatives of monomeric di- or triisocyanates having urethane, urea, carbodiimide, acylurea, isocyanurate, allophanate, biuret, oxadiazinetrione, uretdione and/or iminooxadiazinedione structures is also possible.

The use of polyisocyanates based on aliphatic and/or cycloaliphatic di- or triisocyanates is preferred.

Particularly preferably, the polyisocyanates of component a) are di- or oligomerized aliphatic and/or cycloaliphatic di- or triisocyanates.

Isocyanurates, uretdiones and/or iminooxadiazinediones based on HDI and 1,8-diisocyanato-4-(isocyanatomethyl)octane or mixtures thereof are very particularly preferred.

Likewise, NCO-functional prepolymers having urethane, allophanate, biuret and/or amide groups can be used as component a). Prepolymers of component a) are obtained in a manner well known per se to the person skilled in the art by reacting monomeric, oligomeric or polyisocyanates a1) with isocyanate-reactive compounds a2) in suitable stoichiometry with optional use of catalysts and solvents.

Suitable polyisocyanates a1) are all aliphatic, cycloaliphatic, aromatic or araliphatic di- and triisocyanates known per se to the person skilled in the art, it being unimportant whether these were obtained by means of phosgenation or by phosgene-free processes. In addition, the higher molecular weight subsequent products of monomeric di- and/or triisocyanates having a urethane, urea, carbodiimide, acylurea, isocyanurate, allophanate, biuret, oxadiazinetrione, uretdione or iminooxadiazinedione structure, which are well known per se to a person skilled in the art, can also be used, in each case individually or in any desired mixtures with one another.

Examples of suitable monomeric di- or triisocyanates which can be used as component a1) are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

OH-functional compounds are preferably used as isocyanate-reactive compounds a2) for synthesizing the prepolymers. Said compounds are analogous to the OH-functional compounds as described below for the component b).

Allophanates may also be used as a mixture with other prepolymers or oligomers of component a1). In these cases, the use of OH-functional compounds having functionalities of 1 to 3.1 is advantageous. When monofunctional alcohols are used, those having 3 to 20 carbon atoms are preferred.

It is also possible to use amines for the prepolymer preparation. For example, ethylenediamine, diethylenetriamine, triethylenetetramine, propylenediamine, diaminocyclohexane, diaminobenzene, diaminobisphenyl, difunctional polyamines, for example, the Jeffamines®, amine-terminated polymers having number average molar masses of up to 10 000 g/mol or any desired mixtures thereof with one another are suitable.

For the preparation of prepolymers containing biuret groups, an excess of isocyanate is reacted with amine, a biuret group forming. In this case, suitable amines for the reaction with the di-, tri- and polyisocyanates mentioned are all oligomeric or polymeric, primary or secondary, difunctional amines of the abovementioned type. Examples of these are aliphatic biurets based on aliphatic amines and aliphatic isocyanates, in particular HDI and TMDI.

Preferred prepolymers are urethanes, allophanates or biurets obtained from aliphatic isocyanate-functional compounds and oligomeric or polymeric isocyanate-reactive compounds having number average molar masses of 200 to 10 000 g/mol.

The prepolymers described above preferably have residue contents of free monomeric isocyanate of less than 2% by weight, particularly preferably less than 1.0% by weight, very particularly preferably less than 0.5% by weight.

Of course, the isocyanate component may contain proportionately further isocyanate components in addition to the prepolymers described. It is optionally also possible for the isocyanate component a) proportionately to contain isocyanates which have been partly reacted with isocyanate-reactive ethylenically unsaturated compounds.

It is optionally also possible for the abovementioned isocyanate component a) to contain, completely or proportionately, isocyanates which have been reacted completely or partly with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-di-methylpyrazole, ε-caprolactam, N-tert-butylbenzylamine, cyclopentanone carboxyethyl ester or any desired mixtures of these blocking agents.

In principle, all polyfunctional, isocyanate-reactive compounds which have on average at least 1.5 isocyanate-reactive groups per molecule can be used as component b).

Isocyanate-reactive groups in the context of the present invention are preferably hydroxy, amino or thio groups; hydroxy compounds are particularly preferred.

Suitable polyfunctional, isocyanate-reactive compounds are, for example, polyester, polyether, polycarbonate, poly (meth)acrylate and/or polyurethane polyols.

In addition, aliphatic, araliphatic or cycloaliphatic di-, tri- or polyfunctional alcohols having low molecular weights, i.e. having molecular weights of less than 500 g/mol, and short chains, i.e. containing 2 to 20 carbon atoms, are also suitable as polyfunctional, isocyanate-reactive compounds as constituents of component b).

These may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butyl-propanediol, trimethylpentanediol, positional isomers of diethyloctanediol, 1,3-butylene glycol, cyclohexanediol, 1,4-cyclo-hexanedimethanol, 1,6-hexanediol, 1,2- and 1,4-cyclohexanediol, hydrogenated bisphenol A (2,2-bis(4-hydroxycyclohexyl)propane), 2,2-dimethyl-3-hydroxypropionic acid (2,2-dimethyl-3-hydroxypropyl ester). Examples of suitable triols are trimethylolethane, trimethylolpropane or glycerol. Suitable higher-functional alcohols are ditrimethylolpropane, pentaerythritol, dipentaerythritol or sorbitol.

Suitable polyester polyols are, for example, linear polyester diols or branched polyester polyols, as are obtained in a known manner from aliphatic, cycloaliphatic or aromatic di- or polycarboxylic acids or their anhydrides with polyhydric alcohols having an OH functionality of ≥2. Preferred polyester polyols are based on aliphatic alcohols and mixtures of aliphatic and aromatic acids and have number average molar masses between 500 and 10 000 g/mol and functionalities between 1.8 and 6.1.

The polyester polyols may also be based on natural raw materials, such as castor oil. It is also possible for the polyester polyols to be based on homo- or copolymers of lactones, as can preferably be obtained by an addition reaction of lactones or lactone mixtures in a ring-opening lactone polymerization, such as butyrolactone, ε-caprolactone and/or methyl-ε-caprolactone, with hydroxy-functional compounds, such as polyhydric alcohols having an OH functionality of ≥2 or polyols having a functionality of greater than 1.8, for example of the abovementioned type.

Examples of polyols which are used as starters here are polyether polyols having a functionality of 1.8 to 3.1 and number average molar masses of 200 to 4000 g/mol; poly(tetrahydrofurans) having a functionality of 1.9 to 2.2 and number average molar masses of 500 to 2000 g/mol are preferred. As adducts are butyrolactone, ε-caprolactone and/or methyl-ε-caprolactone, ε-caprolactone is particularly preferred.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols mentioned in the context of the polyester segments and having an OH functionality of ≥2, preferably 1,4-butanediol, 1,6-hexanediol and/or 3-methylpentanediol, or polyester polyols can be converted into polycarbonate polyols.

Suitable polyether polyols are polyadducts of cyclic ethers with OH- or NH-functional starter molecules, which polyadducts optionally have a block structure.

Suitable cyclic ethers are, for example, styrene oxides, ethylene oxide, propylene oxide, tetrahydrofuran, butylene oxide, epichlorohydrin and any desired mixtures thereof.

Starters which may be used are the polyhydric alcohols mentioned in the context of the polyester polyols and having an OH functionality of ≥2 and primary or secondary amines and amino alcohols.

Preferred polyether polyols are those of the abovementioned type, exclusively based on propylene oxide or random or block copolymers based on propylene oxide with further 1-alkylene oxides, the proportion of the 1-alkylene oxide not being higher than 80% by weight. Propylene oxide homopolymers and random or block copolymers which have oxyethylene, oxypropylene and/or oxybutylene units are particularly preferred, the proportion of the oxypropylene units, based on the total amount of all oxyethylene, oxypropylene and oxybutylene units, accounting for at least 20% by weight, preferably at least 45% by weight. Here, oxypropylene and oxybutylene comprise all respective linear and branched C3- and C4-isomers.

Preferably used special polyether polyols are those which consist of an isocyanate-reactive component comprising hydroxy-functional multiblock copolymers of the type $Y(X_i-H)_n$ with i=1 to 10 and n=2 to 8 and number average molecular weights of greater than 1500 g/mol, the segments $X_i$ each being composed of oxyalkylene units of the formula (I), $$-CH_2-CH(R)-O- \qquad \text{formula (I)}$$

in which R is a hydrogen, alkyl, or aryl radical which can also be substituted or may be interrupted by heteroatoms (such as ether oxygens), Y is the underlying starter and the proportion of the segments $X_i$, based on the total amount of the segments $X_i$ and Y, accounts for at least 50% by weight.

In formula (I), R is preferably a hydrogen, a methyl, butyl, hexyl or octyl group or an alkyl radical containing ether groups. Preferred alkyl radicals containing ether groups are those based on oxyalkylene units.

The multiblock copolymers $Y(X_i-H)_n$ preferably have number average molecular weights of more than 1200 g/mol, particularly preferably more than 1950 g/mol, but preferably not more than 12 000 g/mol, particularly preferably not more than 8000 g/mol.

Preferably used block copolymers of the structure $Y(X_i-H)_n$ consist of more than 50 percent by weight of the blocks $X_i$ described above and have a number average total molar mass of greater than 1200 g/mol.

Preferred combinations of component a) and b) in the preparation of the matrix polymers are:

A) Adducts of butyrolactone, ε-caprolactone and/or methyl-ε-caprolactone with polyether polyols having a functionality of 1.8 to 3.1 and number average molar masses of 200 to 4000 g/mol in combination with isocyanurates, uretdiones, iminooxadiazinediones and/or other oligomers based on HDI. Particularly preferably adducts of ε-caprolactone with poly(tetrahydrofurans) having a functionality of 1.9 to 2.2 and number average molar masses of 500 to 2000 g/mol (in particular 600 to 1400 g/mol), the number average total molar mass of which is from 800 to 4500 g/mol, in particular from 1000 to 3000 g/mol, in combination with oligomers, isocyanurates and/or iminooxadiazinediones based on HDI.

B) Polyether polyols having number average molar masses of 500 to 8500 g/mol and OH functionalities of 1.8 to 3.2, exclusively based on propylene oxide, or random or block copolyols based on propylene oxide and ethylene oxide, the proportion of ethylene oxide not being higher than 60% by weight, in combination with urethanes, allophanates or biurets obtained from aliphatic isocyanate-functional compounds and oligomeric or polymeric isocyanate-reactive compounds having number average molar masses of 200 to 6000 g/mol. Propylene oxide homopolymers having number average molar masses of 1800 to 4500 g/mol and OH functionalities of 1.9 to 2.2 in combination with allophanates obtained from HDI or TMDI and difunctional polyether polyols (in particular polypropylene glycols) having number average molar masses of 200 to 2100 g/mol are particularly preferred.

C) Polyether block or multiblock copolymers of the formula (I), in which Y is a purely aliphatic polycarbonate polyol or a polymer of tetrahydrofuran having in each case an OH functionality of 1.8 to 3.1 and a number average molar masses of 400 to 2000 g/mol, n is 2, i is 1 or 2 and R is methyl or H, having a total number average molar mass of 1950 to 9000 g/mol, in combination with urethanes, allophanates or biurets obtained from aliphatic isocyanate-functional compounds and oligomeric or polymeric isocyanate-reactive compounds having number average molar masses of 200 to 6000 g/mol or in combination with isocyanurates, uretdiones, iminooxadiazinediones and/or other oligomers based on HDI. Polyether block or multiblock copolymers of the formula (I), in which Y is a purely aliphatic polycarbonate polyol based on 1,4-butanediol and/or 1,6-hexanediol with dimethyl or diethyl carbonate or a polymer of tetrahydrofuran having an OH functionality of 1.8 to 2.2 and a number average molar masses of 600 to 1400 g/mol (in particular up to 1000 g/mol), n is 2, i is 1 or 2 and R is methyl or H, the proportion of ethylene oxide units, based on the total mass of $X_i$, not being higher than 60% by weight, in combination with allophanates obtained from HDI or TMDI and difunctional polyether polyols (in particular polypropylene glycols) having number average molar masses of 200 to 2100 g/mol, in combination with biurets having number average molar masses of 200 to 1400 g/mol (in particular also as a mixture with other oligomers of difunctional aliphatic isocyanates), based on aliphatic diamines or polyamines and aliphatic diisocyanates, in particular HDI and TMDI, in combination with urethanes obtained from HDI or TMDI and based on adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms), having number average molar masses of 200 to 3000 g/mol, particularly preferably of 1000 to 2000 g/mol (in particular as a mixture with other oligomers of difunctional aliphatic isocyanates) or in combination with isocyanurates, iminooxadiazinediones and/or other oligomers based on HDI are particularly preferred.

One or more different compounds which have groups reacting under the action of actinic radiation with ethylenically unsaturated compounds with polymerization (radiation-curing groups) and are themselves free of NCO groups are used as component B). The writing monomers acrylates and/or methacrylates are preferred.

In component B), compounds such as α,β-unsaturated carboxylic acid derivatives, such as acrylates, methacrylates, maleates, fumarates, maleimides, acrylamides, furthermore vinyl ethers, propenyl ethers, allyl ethers and compounds containing dicyclopentadienyl units and olefinically unsaturated compounds, such as, for example, styrene, α-methylstyrene, vinyltoluene, olefins, such as, for example, 1-octene and/or 1-decene, vinyl esters, (meth)acrylonitrile, (meth) acrylamide, methacrylic acid, acrylic acid, can be used. Acrylates and methacrylates are preferred.

In general, esters of acrylic acid or methacrylic acid are designated as acrylates and methacrylates, respectively. Examples of acrylates and methacrylates which can be used are methyl acrylate, methyl methacrylate, ethyl acrylate, ethyl methacrylate, ethoxyethyl acrylate, ethoxyethyl methacrylate, n-butyl acrylate, n-butyl methacrylate, tert-butyl acrylate, tert-butyl methacrylate, hexyl acrylate, hexyl methacrylate, 2-ethylhexyl acrylate, 2-ethylhexyl methacrylate, butoxyethyl acrylate, butoxyethyl methacrylate, lauryl acrylate, lauryl methacrylate, isobornyl acrylate, isobornyl methacrylate, phenyl acrylate, phenyl methacrylate, p-chlorophenyl acrylate, p-chlorophenyl methacrylate, p-bromophenyl acrylate, p-bromophenyl methacrylate, 2,4,6-trichlorophenyl acrylate, 2,4,6-trichlorophenyl methacrylate, 2,4,6-tribromophenyl acrylate, 2,4,6-tribromophenyl methacrylate, pentachlorophenyl acrylate, pentachlorophenyl methacrylate, pentabromophenyl acrylate, pentabromophenyl methacrylate, pentabromobenzyl acrylate, pentabromobenzyl methacrylate, phenoxyethyl acrylate, phenoxyethyl methacrylate, phenoxyethoxyethyl acrylate, phenoxyethoxyethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, propane-2,2-diylbis[(2,6-dibromo-4,1-phenylen)oxy(2-{[3,3,3-tris(4-chlorophenyl) propan-yl]oxy}propane-3,1-diyl)oxyethane-2,1-diyl] diacrylate, bisphenol A diacrylate, bisphenol A dimethacrylate, tetrabromobisphenol A diacrylate, tetrabromobisphenol A dimethacrylate and the ethoxylated analogue compounds thereof, N-carbazolyl acrylates to mention but a selection of acrylates and methacrylates which can be used.

Of course, urethane acrylates can also be used as component B). Urethane acrylates are understood as meaning compounds having at least one acrylate group which additionally have at least one urethane bond. It is known that such compounds can be obtained by reacting a hydroxy-functional acrylate with an isocyanate-functional compound.

Acrylates and methacrylates having a refractive index $n_D^{20}$ (as measured at a wavelength of 405 nm) of greater than 1.450 are preferably used. Acrylates which contain at least one aromatic structural unit and have a refractive index $n_D^2$ (405 nm) of greater than 1.500 are particularly preferably used.

Acrylates and methacrylates based on bisphenol A or derivatives thereof and those acrylates and methacrylates which contain a thioaryl group may be mentioned as particularly suitable examples thereof.

Examples of the urethane acrylates and/or urethane methacrylates used as component B) are the adducts of aromatic triisocyanates (very particularly preferably tris(4-phenylisocyanato)thiophosphate, or trimers of aromatic diisocyanates, such as toluene diisocyanate) with hydroxyethyl acrylate, hydroxypropyl acrylate, 4-hydroxybutyl acrylate, the adducts of 3-thiomethylphenyl isocyanate with hydroxyethyl acrylate, hydroxypropyl acrylate, 4-hydroxybutyl acrylate and unsaturated glycidyl ether acrylate urethanes (as described in the applications WO 2008/125229 A1 and in the non-prior-published application EP 09009651.2) or any desired mixtures thereof with one another.

Furthermore, the use of glycidyl ether acrylate urethanes as writing monomers is preferred. These comply with the general formula (IIa) or (IIb) or mixtures of (IIa) and (IIb)

in which
n is a natural number from 2 to 6
R' is a mono- or polynuclear organic radical containing aromatic groups and having 4 to 36 carbon atoms,
R" is an olefinically unsaturated radical having 3 to 30 carbon atoms and
R''' is an organic radical derived from an aliphatic or aromatic di- or polyisocyanate and having 2 to 30 carbon atoms.

The unsaturated glycidyl ether acrylate urethanes of the formula IIa or IIb can be prepared in a 2-stage synthesis. In the first reaction, an unsaturated carboxylic acid is reacted with an epoxide, a mixture of two alcohols being formed. Of course, it is also possible in this reaction step to react unsaturated epoxides with any desired carboxylic acids to give the analogous intermediate. In a second reaction step, this alcohol mixture is urethanized by means of a di- or polyisocyanate R'''(NCO)$_n$ of functionality n to give the glycidyl ether acrylate urethane (as described in non-prior-published application EP 09002180.9). Methacrylic acid and acrylic acid or derivatives thereof or aromatic carboxylic acids are preferably used for the reaction with an unsaturated epoxide, aromatic or unsaturated epoxides, such as phenyl, dibromophenyl, naphthyl or biphenyl glycidyl ether or glydidyl (meth)acrylate, are preferably used as epoxides and toluene diisocyanate (TDI), hexamethylene diisocyanate (HDI) or triisocyanatononane (TIN) is preferably used as the isocyanate component.

In a very particularly preferred embodiment, the combinations of (acrylic acid, biphenyl glycidyl ether and TDI), (acrylic acid, phenyl glycidyl ether and TDI) and (acrylic acid, biphenyl glycidyl ether and HDI) are used.

A further preferred embodiment uses, as writing monomers, a combination of a monofunctional and a polyfunctional writing monomer.

The monofunctional writing monomer may have in particular the general formula (II)

(II)

in which $R^1$, $R^2$, $R^3$, $R^4$, $R^5$, in each case independently of one another, are a hydrogen or halogen atom or a C1-C6-alkyl, trifluoromethyl, C1-C6-alkylthio, C1-C6-alkylseleno, C1-C6-alkyltelluro or nitro group, with the proviso that at least one substituent of the group $R^1$, $R^2$, $R^3$, $R^4$, $R^5$ is not hydrogen, $R^6$, $R^7$, in each case by themselves, are hydrogen or a C1-C6-alkyl group and A is a saturated or unsaturated or linear or branched C1-C6-alkyl radical or a polyethylene oxide radical or a polypropylene oxide radical having in each case 2-6 repeating units in the polymer chain, and the monofunctional writing monomer preferably has a glass transition temperature $T_G$ of <0° C. and preferably a refractive index of >1.50 at 405 nm.

The polyfunctional writing monomer may have, in particular, the general formula (III)

(III)

in which n is ≥2 and n is ≤4 and $R^8$, $R^9$ are hydrogen and/or, independently of one another, linear, branched, cyclic or heterocyclic organic radicals which are unsubstituted or optionally also substituted by heteroatoms. Furthermore, the polyfunctional writing monomer may preferably have a refractive index of >1.50 at 405 nm.

One or more photoinitiators are used as component C). The photoinitiator system used can preferably comprise an anionic, cationic or neutral dye and a coinitiator. Examples of these are mixtures of tetrabutylammonium triphenylhexylborate, tetrabutylammonium triphenylbutylborate, tetrabutylammonium trinaphtylbutylborate, tetrabutylammonium tris(4-tert-butyl)phenylbutylborate, tetrabutylammonium tris(3-fluorophenyl)hexylborate and tetrabutylammonium tris(3-chloro-4-methylphenyl)hexylborate with dyes such as, for example, astrazone orange G, methylene blue, new methylene blue, azur A, pyrillium I, safranine O, cyanine, gallocyanine, brilliant green, crystal violet, ethyl violet and thionine.

Further constituents of the photopolymer formulation as component E) may be: free radical stabilizers, optionally catalysts or other auxiliaries and additives.

Inhibitors and antioxidants, as described, for example, in "Methoden der organischen Chemie [Methods of Organic Chemistry]" (Houben-Weyl), 4th Edition, Vol. XIV/1, page 433 et seq., Georg Thieme Verlag, Stuttgart 1961, are suitable as examples of free radical stabilizers. Suitable classes of substances are, for example, phenols, such as, for example, 2,6-di-tert-butyl-4-methylphenol, cresols, hydroquinones, benzyl alcohols, such as, for example, benzhydrol, optionally also quinones, such as, for example, 2,5-di-tert-butylquinone, optionally also aromatic amines such as diisopropylamine or phenothiazine.

2,6-Di-tert-butyl-4-methylphenol, phenothiazine, p-methoxyphenol, 2-methoxy-p-hydroquinone and benzhydrol are preferred.

Optionally, one or more catalysts may be used. These are catalysts for accelerating the urethane formation. Known catalysts for this purpose are, for example, tin octoate, zinc octoate, dibutyltin dilaurate, dimethylbis[(1-oxoneodecyl)oxy]stannane, dimethyltin dicarboxylate, zirconium bis(ethylhexanoate), zirconium acetylacetonate or tertiary amines, such as, for example, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido(1,2-a)pyrimidine.

Dibutyltin dilaurate, dimethylbis[(1-oxoneodecyl)oxy]stannane, dimethyltin dicarboxylate, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido(1,2-a)pyrimidine are preferred.

Of course, further auxiliaries or additives can optionally be used. These may be, for example, additives customary in the area of coating technology, such as solvents, plasticizers, levelling agents or adhesion promoters. It can also be advantageous to use a plurality of additives of one type simultaneously. Of course, it may also be advantageous to use a plurality of additives of a plurality of types.

It is preferably intended for the photopolymer formulation specifically not to contain photopolymerizable additives (component D). The additives may in particular be urethanes and/or fluorinated urethanes.

The urethanes can preferably have the general formula (IV)

(IV)

in which n is ≥1 and n is ≤8 and $R^{10}$, $R^{11}$, $R^{12}$ are hydrogen and/or, independently of one another, linear, branched, cyclic or heterocyclic organic radicals which are unsubstituted or optionally also substituted by heteroatoms, preferably at least one of the radicals $R^{10}$, $R^{11}$, $R^{12}$ being substituted by at least one fluorine atom and $R^{10}$ being particularly preferably an organic radical having at least one fluorine atom.

The fluorourethanes may have a fluorine content of 10-80% by weight of fluorine, preferably of 13-70% by weight of fluorine and particularly preferably 17.5-65% by weight of fluorine.

A film comprising the photopolymer formulation can be applied to a substrate film, for example with the aid of a roll coating unit.

This can be effected by a combination of different process steps in which positive metering pumps known to the person skilled in the art, vacuum devolatilizers, plate filters, static mixers, slot nozzles and various knifecoating systems, single-roll unwinders, dryers, dry lamination device and a single-roll winding device are used. In particular, a coating devices which have, for example, slot nozzles and knifecoating systems are suitable for the application of liquid photopolymer formulations to moving substrate materials and are distinguished by high accuracy in the applied layer thickness.

In a preferred embodiment, the process for coating the substrate film comprises the following individual steps for the treatment of abovementioned photopolymer formulations:
I. transport and metering firstly of the component a), optionally mixed with one or more of the components B), C), D) and E), and secondly, separately therefrom, of the component b), optionally mixed with one or more of the components B), C), D) and E)
II. devolatilization of the streams transported, metered and optionally premixed according to I)
III. filtration of the mixture obtained according to II)
IV. homogenization of the mixture obtained according to III)
V. unwinding and pre-treatment of the substrate film
VI. coating of the substrate film with the mixture obtained according to step IV)
VII. drying of the film coated according to VI)
VIII. lamination of the coated film obtained according to VII)
IX. winding up of the laminated film obtained according to VIII)

In a particularly preferred embodiment, the metering of the starting materials is effected either by gear pumps or by eccentric screw pumps. Centrifugal devolatilizers are used for devolatilization of the starting materials and plate filters for filtration. The mixing of the individual components is effected by a static mixer with appropriately designed mixing geometry, such as, for example, length and diameter. A preferably used coating unit is a slot die. The coated material is dried via air dryers with the desired air temperature and moisture content over a defined period.

FIG. 1 shows a schematic setup of a typical coating unit, including arrangement of the pre-treatment of the coating material (1-5), schematic path of the substrate film (8+9), coating device for application to the substrate film (6) and subsequent drying process (7).

Figure 2:
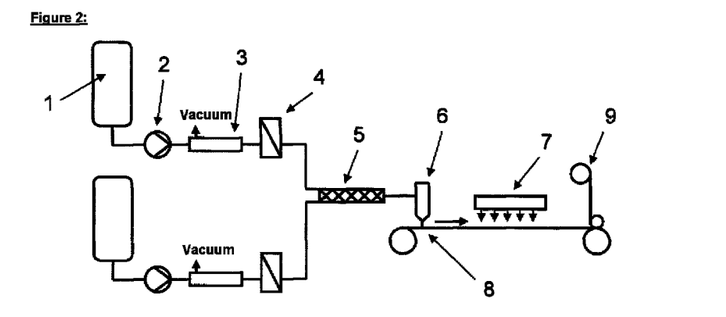
FIG. 2 illustrates a schematic setup of a typical coating unit.

In FIG. 2, the reference numerals represent the following components:

| | |
|---|---|
| 1 | Storage container |
| 2 | Metering device |
| 3 | Vacuum devolatilization |
| 4 | Filter |
| 5 | Static mixer |
| 6 | Coating device |
| 7 | Dryer |
| 8 | Web path |
| 9 | Product lamination |

By combining the process steps described, as shown in FIG. 2, photopolymer formulations may be applied on moving substrate materials in a high accuracy of layer thickness.

According to a further preferred embodiment, the holographic media may be film composites which may consist of one or more substrate films, one or more photopolymer layers and one or more protective films in any desired arrangement.

Preferred materials or material composites of the substrate layer are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide, polymethyl methacrylate, polyvinyl chloride, polyvinyl butyral or polydicyclopentadiene or mixtures thereof. In addition, material composites, such as film laminates or coextrudates, can be used as substrate film. Examples of material composites are duplex and triplex films having a structure according to one of the schemes A/B, A/B/A or A/B/C, such as PC/PET, PET/PC/PET and PC/TPU (TPU=thermoplastic polyurethane). PC and PET are particularly preferably used as substrate film.

In addition to the constituents and can for the film composite have one or more covering layers on the photopolymer layer in order to protect it from dirt and environmental influences. Plastics films or film composite systems, but also clearcoats can be used for this purpose.

In addition, further protective layers, for example a backing of the substrate film, may be used.

The invention furthermore relates to a holographic medium obtainable by the process according to the invention.

EXAMPLES

The following examples serve for explaining the invention. Unless noted otherwise, all stated percentages are based on percent by weight.

Designations which are Used Below:
Photopolymer formulations comprising:
three-dimensionally crosslinked matrix polymers A). Particularly preferred three-dimensionally crosslinked organic polymers are those which are composed of
an isocyanate component a)
and an isocyanate-reactive component b) as precursors and
are crosslinked with the aid of a catalyst component E) which as a rule is added in solution,
writing monomers B) which have groups which react under the action of actinic radiation with ethylenically unsaturated compounds with polymerization (radiation-curing groups) and are dissolved or distributed in this matrix
at least one photoinitiator system C)
optionally a non-photopolymerizable component D)
optionally catalysts, free radical stabilizers, solvents, additives and other auxiliaries and/or additives E)

Starting Materials

Isocyanates Used (Components a)
Isocyanate component 1 (component a1) is an experimental product of Bayer MaterialScience AG, Leverkusen, Germany, hexane diisocyanate-based polyisocyanate, proportion of iminooxadiazinedione at least 30%, NCO content: 23.5% (Bayer trade name Desmodur® N 3900)

Isocyanate component 2 (component a2) is an experimental product of Bayer MaterialScience AG, Leverkusen, Germany, full allophanate of hexane diisocyanate on polypropylene glycol having a number average molar mass of about 280 g/mol, NCO content: 16.5-17.3%. (Bayer trade name Desmodur® XP 2747)

Isocyanate component 3 (component a3) is a commercially available product of Bayer MaterialScience AG, Leverkusen, Germany, mixture of 29.4 mol % of isocyanurate based on HDI with 70.6 mol % of the urethane of poly(ε-caprolactone) having a number average molar mass of 650 g/mol with HDI, NCO content 10.5-11.5%. (Bayer trade name Desmodur® N 3800)

Isocyanate-Reactive Components Used (Component b)
Polyol 1 (component b1) is an experimental product of Bayer MaterialScience AG, Leverkusen, Germany; the preparation is described below.

Polyol 2 (component b2) is an experimental product of Bayer MaterialScience AG, Leverkusen, Germany; the preparation is described below.

Polyol 3 (component b3) is an experimental product of Bayer MaterialScience AG, Leverkusen, Germany; the preparation is described below.

Terathene® 650 is a commercially available product of BASF SE, Ludwigshafen, Germany (Poly-THF having molar masses of 650 g/mol).

Radiation-Curing Compound Used (Component B)

Acrylate 1 (component B1) is an experimental product of Bayer MaterialScience AG, Leverkusen, Germany, the preparation is described below.

Acrylate 2 (component B2) is an experimental product of Bayer MaterialScience AG, Leverkusen, Germany, the preparation is described below.

Acrylate 3 (component B3) is an experimental product of Bayer MaterialScience AG, Leverkusen, Germany, the preparation is described below.

Components of the Photoinitiator Systems Used (Component C)

Coinitiator 1 tetrabutylammonium tris(3-chloro-4-methylphenyl)(hexyl)borate, [1147315-11-4] is an experimental product produced by Ciba Inc., Basel, Switzerland.

Dye 1 is new methylene blue (CAS1934-16-3) and was obtained from SIGMA-ALDRICH CHEMIE GmbH, Steinheim, Germany.

Dye 2 is safranine O (CAS 477-73-6) and was obtained from SIGMA-ALDRICH CHEMIE GmbH, Steinheim, Germany.

Dye 3 is ethyl violet (CAS 2390-59-2) and was obtained in 80% purity from SIGMA-ALDRICH CHEMIE GmbH, Steinheim, Germany, and used in this form.

Dye 4 is astrazone orange G (CAS 3056-93-7) and was obtained from SIGMA-ALDRICH CHEMIE GmbH, Steinheim, Germany.

Non-Photopolymerizable Components Used (Component D)

The non-photopolymerizable components (component D1 to D10) are experimental products of Bayer MaterialScience AG, Leverkusen, Germany, the preparation of which is described below.

Catalyst Used (Component E)

Catalyst 1 (component E1): Urethanization catalyst, dimethylbis[(1-oxoneodecyl)oxy]-stannane, commercially available product of Momentive Performance Chemicals, Wilton, Conn., USA (used as 10% strength solution in N-ethylpyrrolidone).

Auxiliaries and Additives Used (Component E)

BYK 310: Silicone-based surface additive of BYK-Chemie GmbH, Wesel, Germany (component E2) (25% strength solution in xylene)

DMC catalyst: double metal cyanide catalyst based on zinc hexacyanocobaltate (III), obtainable by the process described in EP-A 700 949.

Irganox 1076 is octadecyl 3,5-di-(tert)-butyl-4-hydroxyhydrocinnamate (CAS 2082-79-3).

Methods of Measurement:

The stated OH numbers were determined according to DIN 53240-2.

The stated NCO values (isocyanate contents) were determined according to DIN EN ISO 11909.

For the determination of the viscosity, the component or mixture to be investigated was applied in a cone-on-plate measuring system of a rheometer (from Anton Paar Physica Model MCR 51), at 20° C. The measurement is carried out under the following conditions:

Measuring body: cone CP 25, d=25 mm, angle=1°

Measuring gap as distance between cone and plate: 0.047 mm

Duration of measurement: 10 sec.

Determination of viscosity at a shear rate of 250 l/sec.

Determination of the TGA 95 Value

The TGA 95 values of the individual components can be determined by weighing an amount of about 10 mg of the sample of the respective component into a small aluminium pan having a volume of 70 µl introducing the small aluminium pan an oven of a thermobalance, preferably a TG50 thermobalance from Mettler-Toledo, and measuring the loss of mass of the sample in the open small aluminium pan at a constant oven heating rate of 20 K/min, the start temperature of the oven being 30° C. and the end temperature 600° C., flushing the oven with a 200 ml/min nitrogen stream during the determination and determining, as a TGA 95 value of the respective component, the temperature at which a loss of mass of the sample of 5% by weight, based on the originally weighed in amount of sample, has occurred.

Measurement of the Holographic Properties DE and $\Delta n$ of the Holographic Media by Means of Two-Beam Interference in a Reflection Arrangement For measuring the holographic performance, the protective film of the holographic film is peeled off and the holographic film is laminated on the photopolymer side onto a 1 mm thick glass plate suitable in length and width using a rubber roller with gentle pressure. This sandwich comprising glass and photopolymer film can now be used to determine the holographic performance parameters DE and $\Delta n$.

The beam of an He—Ne laser (emission wavelength 633 nm) was converted with the aid of the spatial filter (SF) and together with the collimation lens (CL) into a parallel homogenous beam. The final cross sections of the signal and reference beam are established by the iris diaphragms (I). The diameter of the iris diaphragm opening is 0.4 cm. The polarization-dependent beam splitters (PBS) split the laser beam into two coherent equally polarized beams. Via the $\lambda/2$ plates, the power of the reference beam was adjusted to 0.5 mW and the power of the signal beam to 0.65 mW. The powers were determined using the semiconductor detectors (D) with sample removed. The angle of incidence ($\alpha_0$) of the reference beam is $-21.8°$ and the angle of incidence ($\beta_0$) of the signal beam is $41.8°$. The angles are measured starting from the sample normal to the beam direction. According to FIG. 3, $\alpha_0$ therefore has a negative sign and $\beta_0$ a positive sign. At the location of the sample (medium), the interference field of the two overlapping beams produced a grating of light and dark strips which are perpendicular to the angle bisector of the two beams incident on the sample (reflection hologram). The strip spacing $\Lambda$, also referred to as grating period, in the medium is ~225 nm (the refractive index of the medium assumed to be ~1.504).

Figure 3:
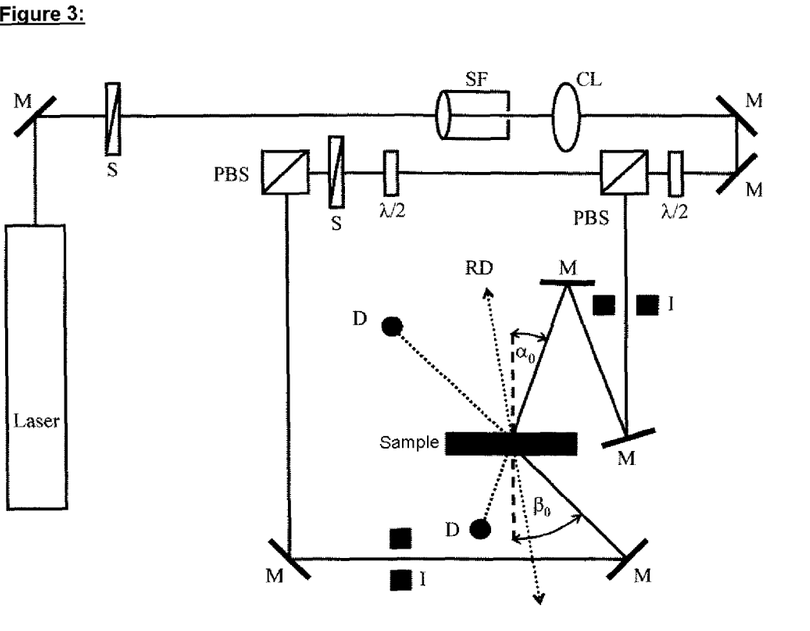
FIG. 3 illustrates a holographic experimental setup to measure the diffraction efficiency (DE) of a media.

FIG. 3 shows the holographic experimental setup with which the diffraction efficiency (DE) of the media was measured.

Holograms were written into the medium in the following manner:

Both shutters (S) are opened for the exposure time t.

Thereafter, with closed shutters (S), the medium was allowed a time of 5 minutes for the diffusion of the still unpolymerized writing monomers.

The recorded holograms were read in the following manner. The shutter of the signal beam remained closed. The shutter of the reference beam was opened. The iris diaphragm of the reference beam was closed to a diameter of <1 mm. This ensured that the beam was always completely in the previously written hologram for all angles ($\Omega$) of rotation of the medium. The turntable, under computer control, covered the angle range from $\Omega_{min}$ to $\Omega_{max}$ with an angle step width of 0.05° C. $\Omega$ is measured from the sample normal to the reference direction of the turntable. The reference direction of the turntable occurs when, during recording of the hologram, the angle of incidence of the reference beam and of the signal beam are of equal magnitude, i.e. $\alpha_0 = -31.8°$ and $\beta_0 = 31.8°$. $\Omega_{recording}$ is then 0°. For $\alpha_0 = -21.8°$ and $\beta_0 = 41.8°$, $\Omega_{recording}$ is therefore 10°. The following is generally true for the interference field during recording of the hologram:

$$\alpha_0 = \theta_0 + \Omega_{recording}.$$

$\theta_0$ is the semiangle in the laboratory system outside the medium and the following is true during recording of the hologram:

$$\theta_0 = \frac{\alpha_0 - \beta_0}{2}.$$

In this case, $\theta_0$ is therefore $-31.8°$. At each angle $\Omega$ of rotation approached, the powers of the beam transmitted in the zero order were measured by means of the corresponding detector D and the powers of the beam diffracted in the first order were measured by means of the detector D. At each angle $\Omega$ approached, the diffraction efficiency was obtained as the quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve (it describes the diffraction efficiency $\eta$ as a function of the angle $\Omega$ of rotation of the recorded hologram) was measured and was stored in a computer. In addition, the intensity transmitted in the zero order was also plotted against the angle $\Omega$ of rotation and was stored in a computer.

The maximum diffraction efficiency (DE=$\eta_{max}$) of the hologram, i.e. its peak value, was determined at $\Omega_{reconstruction}$. For this purpose, the position of the detector of the diffracted beam was changed if necessary, in order to determine this maximum value.

The refractive index contrast $\Delta n$ and the thickness d of the photopolymer layer were now determined by means of the coupled wave theory (c.f. H. Kogelnik, The Bell System Technical Journal, Volume 48, November 1969, Number 9 page 2909-page 2947) from the measured Bragg curve and the angle variation of the transmitted intensity. It should be noted that, owing to the thickness shrinkage occurring as a result of the photopolymerization, the strip spacing $\Lambda'$ of the hologram and the orientation of the strips (slant) may deviate from the strip spacing $\Lambda$ of the interference pattern and the orientation thereof. Accordingly, the angle $\alpha_0'$ or the corresponding angle of the turntable $\Omega_{reconstruction}$ at which maximum diffraction efficiency is achieved will also deviate from $\alpha_0$ or from the corresponding $\Omega_{recording}$, respectively. As a result, the Bragg condition changes. This change is taken into account in the evaluation method. The evaluation method is described below:

All geometrical quantities which relate to the recorded hologram and not to the interference pattern are represented as dashed quantities.

According to Kogelnik, the following is true for the Bragg curve $\eta(\Omega)$ of a reflection hologram:

$$\eta = \begin{cases} \dfrac{1}{1 - \dfrac{1 - (\xi/v)^2}{\sin^2\left(\sqrt{\xi^2 - v^2}\right)}}, & \text{for } v^2 - \xi^2 < 0 \\ \dfrac{1}{1 + \dfrac{1 - (\xi/v)^2}{\sinh^2\left(\sqrt{v^2 - \xi^2}\right)}}, & \text{for } v^2 - \xi^2 \geq 0 \end{cases}$$

with:

$$v = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

$$\Lambda' = \frac{\lambda}{2 \cdot n \cdot \cos(\psi' - \alpha')}$$

When reading the hologram ("reconstruction"), the situation is analogous to that described above:

$$\theta'_0 = \theta_0 + \Omega$$

$$\sin(\theta'_0) = n \cdot \sin(\theta')$$

At the Bragg condition, the dephasing DP is 0. Accordingly, the following is true:

$$\alpha'_0 = \theta_0 + \Omega_{reconstruction}$$

$$\sin(\alpha'_0) = n \cdot \sin(\alpha')$$

The still unknown angle $\beta'$ can be determined from the comparison of the Bragg condition of the interference field during recording of the hologram and the Bragg condition during reading of the hologram, assuming that only thickness shrinkage takes place. The following is then true:

$$\sin(\beta') = \frac{1}{n} \cdot [\sin(\alpha_0) + \sin(\beta_0) - \sin(\theta_0 + \Omega_{reconstruction})]$$

$v$ is the grating thickness, $\xi$ is the detuning parameter and $\psi'$ is the orientation (slant) of the refractive index grating which was recorded. $\alpha'$ and $\beta'$ correspond to the angles $\alpha_0$ and $\beta_0$ of the interference field during recording of the hologram, but measured in the medium and applicable to the grating of the hologram (after thickness shrinkage). n is the mean refractive index of the photopolymer and was set at 1.504. $\lambda$ is the wavelength of the laser light in vacuo.

The maximum diffraction efficiency (DE=$\eta_{max}$) for $\xi=0$ is then:

$$DE = \tanh^2(v) = \tanh^2\left(\frac{\pi \cdot \Delta n \cdot d'}{\lambda \cdot \sqrt{\cos(\alpha') \cdot \cos(\alpha' - 2\psi)}}\right)$$

Figure 4:
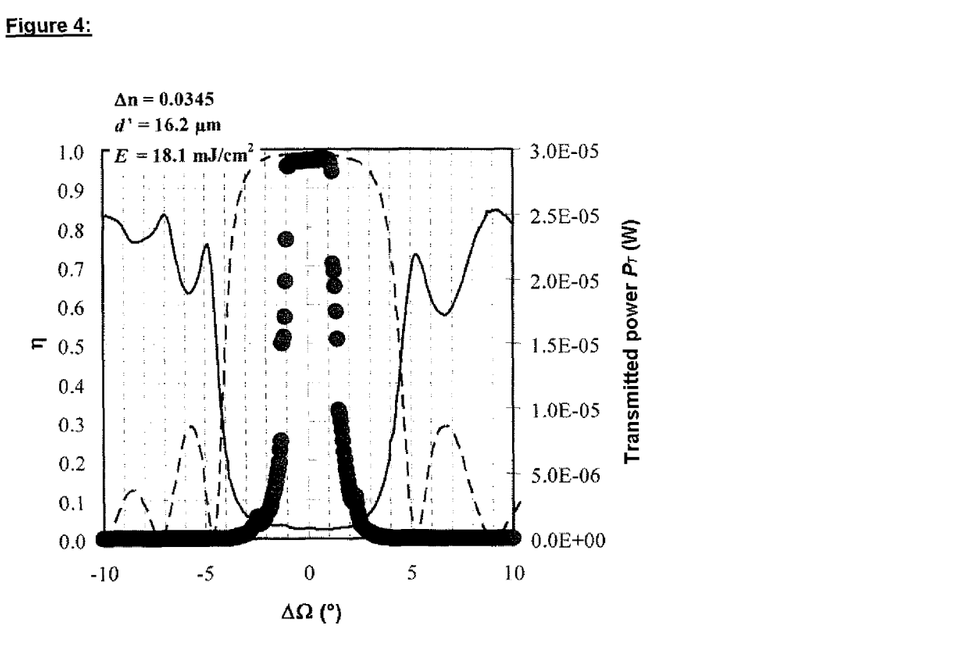
FIG. 4 illustrates a graph showing the measured data of the diffraction efficiency, the theoretical Bragg curve and the transmitted intensity plotted against the angle detuning.

The measured data of the diffraction efficiency, the theoretical Bragg curve and the transmitted intensity are plotted against the centred angle of rotation $\Delta\Omega \equiv \Omega_{reconstruction} - \Omega = \alpha'_0 - \theta'_0$, also referred to as angle detuning, as shown in FIG. 4.

Since DE is known, the shape of the theoretical Bragg curve according to Kogelnik is determined only by the thickness d' of the photopolymer layer. Δn is corrected via DE for a given thickness d' so that measurement and theory of DE always agree. d' is now adjusted until the angular positions of the first secondary minima of the theoretical Bragg curve correspond to the angular positions of the first secondary maxima of the transmitted intensity and in addition the full width at half maximum (FWHM) for the theoretical Bragg curve and for the transmitted intensity correspond.

Since the direction in which a reflection hologram rotates on reconstruction by means of an Ω scan, but the detector for the diffracted light can detect only a finite angular range, the Bragg curve of broad holograms (small d') is not completely registered with an Ω scan, but only the central region, with suitable detector positioning. The shape of the transmitted intensity which is complementary to the Bragg curve is therefore additionally used for adjusting the layer thickness d'.

FIG. 4 shows the plot of the Bragg curve η according to the coupled wave theory (dashed line), of the measured diffraction efficiency (solid circles) and of the transmitted power (black solid line) against the angle detuning ΔΩ.

For one formulation, this procedure was possibly repeated several times for different exposure times t on different media in order to determine at which mean energy dose of the incident laser beam during recording of the hologram DE becomes the saturation value. The mean energy dose E is obtained as follows from the powers of the two partial beams coordinated with the angles $\alpha_0$ and $\beta_0$ (reference beam with $P_r$=0.50 mW and signal beam with $P_s$=0.63 mW), the exposure time t and the diameter of the iris diaphragm (0.4 cm):

$$E(\text{mJ}/\text{cm}^2) = \frac{2 \cdot [P_r + P_s] \cdot t(s)}{\pi \cdot 0.4^2 \text{cm}^2}$$

The powers of the partial beams were adjusted so that, at the angles $\alpha_0$ and $\beta_0$ used, the same power density is reached in the medium.

As an alternative I, a test equivalent to the setup shown in FIG. 1 was also carried out using a green laser having the emission wavelength λ of 532 nm in vacuo. Here, $\alpha_0$=−11.5° and $\beta_0$=33.5° and $P_r$=1.84 mW and $P_s$=2.16 mW.

As an alternative II, a test equivalent to the setup shown in FIG. 1 was also carried out using a blue laser having the emission wavelength λ of 473 nm in vacuo. Here, $\alpha_0$ is −22.0° and $\beta_0$ is 42.0° and $P_r$ is 1.78 mW and $P_s$ is 2.22 mW.

In examples, in each case the maximum value in Δn is reported, and the doses used are between 4 and 64 mJ/cm² per arm.

Measurement of the Layer Thickness of the Photopolymer Layers

The physical layer thickness was determined using commercially available white light interferometers, such as, for example, the device FTM-Lite NIR layer thickness gauge from Ingenieursbüro Fuchs.

The determination of the layer thickness is based in principle on interference phenomena on thin layers. Light waves which have been reflected by two interfaces of different optical density are superposed to one another. The undisturbed superposition of the reflected partial beams now leads to periodic brightening and extinction in the spectrum of a white continuum radiator (e.g. halogen lamp). This superposition is referred to as interference by the person skilled in the art. These interference spectra are measured and mathematically evaluated.

Preparation of the Components

Preparation of Polyol 1 (Component b1)

In a 1 l flask, 0.18 g of tin octanoate, 374.8 g of ε-caprolactone and 374.8 g of a difunctional polytetrahydrofuran polyether polyol (equivalent weight 500 g/mol OH) are initially introduced and heated to 120° C. and kept at this temperature until the solids content (proportion of non-volatile constituents) was 99.5% by weight or higher. Thereafter, cooling was effected and the product was obtained as a waxy solid.

Preparation of Polyol 2 (Component b2)

2475 g of Terathene® 650 were weighed into a 20 l reaction vessel equipped with a stirrer and 452.6 mg of DMC catalyst were added. Heating to 105° C. was then effected while stirring at about 70 rpm. By applying a vacuum and depressurizing with nitrogen three times, air was exchanged for nitrogen. After the stirrer speed had been increased to 300 rpm, nitrogen was passed through the mixture from below for 57 minutes with the vacuum pump running and at a pressure of about 0.1 bar. Thereafter, a pressure of 0.5 bar was established by means of nitrogen and 100 g of ethylene oxide (EO) and 150 g of PO were passed in simultaneously to initiate the polymerization. As a result, the pressure increased to 2.07 bar. After 10 minutes, the pressure had fallen again to 0.68 bar and a further 5.116 kg of EO and 7.558 kg of PO as a mixture were passed in at 2.34 bar over a period of 1 h 53 min. 31 min after the end of the epoxide metering, a vacuum was provided at a residual pressure of 2.16 bar and complete degassing was effected. The product was stabilized by addition of 7.5 g of Irganox 1076 and was obtained as slightly turbid, viscous liquid (OH number 27.1 mg KOH/g, viscosity at 25° C.: 1636 mPas).

Preparation of Polyol 3 (Component b3)

2465 g of Terathene® 650 were weighed into a 20 l reaction vessel equipped with a stirrer and 450.5 mg of DMC catalyst were added. Heating to 105° C. was then effected while stirring at about 70 rpm. By applying a vacuum and depressurizing with nitrogen three times, air was exchanged for nitrogen. After the stirrer speed had been increased to 300 rpm, nitrogen was passed through the mixture from below for 72 minutes with the vacuum pump running and at a pressure of about 0.1 bar. Thereafter, a pressure of 0.3 bar was established by means of nitrogen and 242 g of propylene oxide (PO) were passed in to initiate the polymerization. As a result, the pressure increased to 2.03 bar. After 8 minutes, the pressure had fallen again to 0.5 bar and a further 12.538 kg of PO were metered in at 2.34 bar over a period of 2 h 11 min. 17 minutes after the end of the PO metering, a vacuum was applied at a residual pressure of 1.29 bar and complete degassing was effected. The product was stabilized by addition of 7.5 g of Irganox 1076 and obtained as a colourless, viscous liquid (OH number: 27.8 mg KOH/g, viscosity at 25° C.: 1165 mPas).

Preparation of Acrylate 1 (Component B1) (phosphorothioyltris(oxy-4,1-phenyleneimino-carbonyloxyethane-2,1-diyl)triacrylate)

0.1 g of 2,6-di-tert-butyl-4-methylphenol, 0.05 g of dibutyltin dilaurate (Desmorapid® Z, Bayer MaterialScience AG, Leverkusen, Germany) and 213.07 g of a 27% strength solution of tris(p-isocyanatophenyl)thiophosphate in ethyl acetate (Desmodur® RFE, product of Bayer MaterialScience AG, Leverkusen, Germany) were initially taken in a 500 ml round-bottomed flask and heated to 60° C. Thereafter, 42.37 g of 2-hydroxyethyl acrylate were added dropwise and the mixture was further kept at 60° C. until the isocyanate content had fallen below 0.1%. Thereafter, cooling was effected and the ethyl acetate was completely removed in vacuo. The product was obtained as a semicrystalline solid.

Preparation of Acrylate 2 (Component B2) 2-({[3-(methylsulphanyl)phenyl]-carbamoyl}oxy)ethyl prop-2-enoate)

0.02 g of 2,6-di-tert-butyl-4-methylphenol, 0.01 g of Desmorapid® Z, 11.7 g of 3-(methylthio)phenyl isocyanate were initially introduced and initially introduced into a 100 ml round-bottomed flask and heated to 60° C. Thereafter, 8.2 g of 2-hydroxyethyl acrylate were added dropwise and the mixture was further kept at 60° C. until the isocyanate content had fallen below 0.1%. Cooling was then effected. The product was obtained as a light yellow liquid.

Preparation of Acrylate 3 (Component B3) (Mixture of (4-methylbenzene-1,3-diyl)-bis [carbamoyloxy-3-(biphenyl-2-yloxy)propane-2,1-diyl]bisacrylate and (4-methylbenzene-1,3-diyl)bis[carbamoyloxy-3-(biphenyl-2-yloxy)propane-1,2-diyl]bisacrylate and Analogous Isomers)

430.2 g of Denacol EX 142 (Nagase-Chemtex, Japan), 129.7 g of acrylic acid, 1.18 g of triphenylphosphine and 0.0056 g of 2,6-di-tert-butyl-4-methylphenol were initially introduced into a three-necked flask having a reflux condenser and stirrer. Air was slowly passed through the mixture and the latter was thermostated at 60° C. Stirring is then effected for 24 hours at 90° C. A clear liquid having an OH number of 157.8 mg KOH/g was obtained. 21.3 g of this intermediate product and 5.2 g of a mixture of 2,4- and 2,6-toluidene diisocyanate (Desmodur T80, Bayer MaterialScience AG, Leverkusen, Germany) were initially introduced into a three-necked flask having a reflux condenser and stirrer. Air was slowly passed through the mixture and the latter was thermostated at 60° C. After an initial exothermic reaction, the product was stirred for 24 hours at 60° C. A clear, colourless, glassy product having NCO of 0% was obtained.

Preparation of Photoinitiator System 1 (Component C1)

In the dark or under suitable lighting, 0.05 g of dye 1, 0.05 g of dye 2, 0.05 g of dye 4, 1.50 g of coinitiator 1 are dissolved in 3.50 g of N-ethylpyrrolidone in a beaker. The corresponding percentages by weight of this solution are used for preparing the example media.

Preparation of Photoinitiator System 2 (Component C2)

In the dark or under suitable lighting, 0.05 g of dye 1, 0.05 g of dye 3, 0.05 g of dye 4, 1.50 g of coinitiator 1 are dissolved in 3.50 g of N-ethylpyrrolidone in a beaker. The corresponding percentages by weight of this solution are used for preparing the example media.

Preparation of Photoinitiator System 3 (Component C3)

In the dark or under suitable lighting, 0.10 g of dye 1, 1.00 g of coinitiator 1 are dissolved in 3.50 g of N-ethylpyrrolidone in a beaker. The corresponding percentages by weight of this solution are used for preparing the example media.

Preparation of the Non-Photopolymerizable Component (Component D1) (bis(2,2,3,3,4,4,5,5,6,6,7,7-dodecafluoroheptyl-1)-(2,2,4-trimethylhexane-1,6-diyl) biscarbamate)

0.02 g of dibutyltin dilaurate (Desmorapid Z, Bayer MaterialScience AG, Leverkusen, Germany) and 3.6 g of 2,4,4-trimethylhexane 1,6-diisocyanate (TMDI) were initially introduced into a 50 ml round-bottomed flask and heated to 60° C. Thereafter, 11.9 g of 2,2,3,3,4,4,5,5,6,6,7,7-dodecafluoroheptan-1-ol were added dropwise and the mixture was further kept at 60° C. until the isocyanate content had fallen below 0.1%. Cooling was then effected. The product was obtained as a colourless oil.

The additives described below in Table 2 (component D2 to D10) were prepared in a manner analogous to that described for the additive (component D1) in the stated compositions.

| Additive | Name | Isocyanate and amount | Alcohol and amount | Catalyst and amount | Temp [° C.] | Description |
|---|---|---|---|---|---|---|
| D2 | 2,2,3,3,4,4,5,5,6,6,7,7,8,8,9,9-Hexadecafluorononyl butylcarbamate | n-Butyl isocyanate 186 g | 2,2,3,3,4,4,5,5,6,6,7,7,8,8,9,9-Hexadecafluorononanol 813 g | Desmorapid Z 0.50 g | 60° C. | colourless liquid |
| D3 | 2,2,2-Trifluoroethyl hexylcarbamate | n-Hexyl isocyanate 55.9 g | Trifluoroethanol 44.0 g | Desmorapid Z 0.05 g | 60° C. | colourless liquid |
| D4 | Bis(1,1,1,3,3,3-hexafluoropropan-2-yl)-(2,2,4-trimethylhexane-1,6-diyl) bis-carbamate | 2,4,4-Trimethylhexane 1,6-diisocyanate (TMDI) 50.0 g | Hexafluoro-2-propanol 80.0 g | Desmorapid Z 0.07 g | 60° C. | colourless liquid |

-continued

| Additive | Name | Isocyanate and amount | Alcohol and amount | Catalyst and amount | Temp [° C.] | Description |
|---|---|---|---|---|---|---|
| D5 | 2,2,3,3,4,4,5,5,6,6,7,7-Dodecafluoroheptyl butylcarbamate | n-Butyl isocyanate 3.44 g | 2,2,3,3,4,4,5,5,6,6,7,7-Dodecafluoroheptan-1-ol 11.54 g | Desmorapid Z 0.02 g | 70° C. | colourless liquid |
| D6 | 2,2,3,3,4,4,5,5,6,6,7,7-Dodecafluoroheptyl hexylcarbamate | n-Hexyl isocyanate 4.15 g | 2,2,3,3,4,4,5,5,6,6,7,7-Dodecafluoroheptan-1-ol 10.84 g | Desmorapid Z 0.02 g | 70° C. | colourless liquid |
| D7 | 2,2,3,3,4,4,5,5,6,6,7,7-Dodecafluoroheptyl propan-2-ylcarbamate | i-Propyl isocyanate 3.06 g | 2,2,3,3,4,4,5,5,6,6,7,7-Dodecafluoroheptan-1-ol 11.93 g | Desmorapid Z 0.02 g | 70° C. | colourless liquid |
| D8 | 2,2,3,3,4,4-Heptafluorobutyl hexylcarbamate | n-Hexyl isocyanate 5.82 g | 2,2,3,3,4,4,4-Heptafluorobutan-1-ol 9.16 g | Desmorapid Z 0.02 g | 70° C. | colourless liquid |
| D9 | 2,2,3,3,4,4,5,5,6,6,7,7,8,8,9,9-Hexadecafluorononyl hexylcarbamate | n-Hexyl isocyanate 3.40 g | 2,2,3,3,4,4,5,5,6,6,7,7,8,8,9,9-Hexadecafluorononan-1-ol 11.6 g | Desmorapid Z 0.02 g | 70° C. | colourless solid |
| D10 | 2,2,3,3,4,4,5,5,6,6,7,7,8,8,9,9-Hexadecafluorononyl cyclohexylcarbamate | Cyclohexyl isocyanate 3.37 g | 2,2,3,3,4,4,5,5,6,6,7,7,8,8,9,9-Hexadecafluorononan-1-ol 11.61 g | Desmorapid Z 0.02 g | 70° C. | colourless solid |

Preparation of the Samples and Example Media

Preparation of the Photopolymer Formulation for the Production of Holographic Films Table 3 lists the investigated examples of the photopolymer formulations which are used for the continuous preparation of holographic films with regard to their composition.

For the preparation of the photopolymer formulation, the photopolymerizable monomers (component B), the nonpolymerizable components D, then Fomrez® UL 28 (component E1) and the surface-active additives BYK 310 (component E2) are added stepwise to the components polyol (component b) and mixed. Thereafter, a solution of the component C of the photopolymer solution is added in the dark and mixed so that a clear solution was obtained. Optionally, the formulation can be heated at 60° C. for a short time in order to promote the solubility of the starting materials. Finally, the corresponding isocyanate component a is added at 30° C. and mixing is effected again. The liquid material obtained is then applied by means of a knife coater or slot die to a 36 μm thick polyethylene terephthalate film and dried for 4.5 minutes at the corresponding drying temperature (cf. example Table 6) in an air-circulation dryer. The photopolymer layer is then covered with a 40 μm thick polyethylene film and is rolled up.

The desired target layer thickness of the dried photopolymers are preferably between 10 and 20 μm. The layer thicknesses achieved for the holographic films produced are shown in Table 6.

The production speeds are preferably in the range from 0.2 m/min to 300 m/min and particularly preferably in the range from 1.0 m/min to 50 m/min.

This type of holographic films is particularly suitable for determining the performance thereof according to the methods described in the section Measurement of the holographic properties DE and Δn of the holographic media by means of two-beam interference in a reflection arrangement.

TABLE 3

Holographic media which were tested with regard to their performance Δn

| Holographic medium | Isocyanate component | Proportion (% by weight) | Isocyanate-reactive component | Proportion (% by weight) | NCO:OH | Photopolymerizable monomer 1 | Proportion (% by weight) | Photopolymerizable monomer 2 | Proportion (% by weight) |
|---|---|---|---|---|---|---|---|---|---|
| M1 | a1 | 6.30 | b1 | 33.80 | 1.02:1 | B1 | 20.0 | B2 | 20.0 |
| M2 | a1 | 6.30 | b1 | 33.80 | 1.02:1 | B1 | 20.0 | B2 | 20.0 |
| M3 | a1 | 6.30 | b1 | 33.80 | 1.02:1 | B1 | 20.0 | B2 | 20.0 |
| M4 | a1 | 6.30 | b1 | 33.80 | 1.02:1 | B1 | 20.0 | B2 | 20.0 |
| M5 | a1 | 6.16 | b1 | 33.23 | 1.02:1 | B1 | 15.0 | B2 | 15.0 |
| M6 | a1 | 6.16 | b1 | 33.23 | 1.02:1 | B1 | 15.0 | B2 | 15.0 |
| M7 | a1 | 6.30 | b1 | 33.80 | 1.02:1 | B1 | 20.0 | B2 | 20.0 |
| M8 | a1 | 6.30 | b1 | 33.80 | 1.02:1 | B1 | 20.0 | B2 | 20.0 |
| M9 | a1 | 6.30 | b1 | 33.80 | 1.02:1 | B1 | 20.0 | B2 | 20.0 |
| M10 | a2 | 4.52 | b3 | 34.93 | 1.02:1 | B1 | 15.0 | B2 | 15.0 |
| M11 | a3 | 6.93 | b2 | 32.27 | 1.02:1 | B1 | 15.0 | B2 | 15.0 |
| M12 | a1 | 6.30 | b1 | 33.80 | 1.02:1 | B1 | 20.0 | B2 | 20.0 |
| M13 | a2 | 4.40 | b2 | 34.85 | 1.02:1 | B1 | 15.0 | B2 | 15.0 |
| M14 | a2 | 4.40 | b2 | 34.85 | 1.02:1 | B1 | 15.0 | B2 | 15.0 |
| M15 | a2 | 4.40 | b2 | 34.85 | 1.02:1 | B1 | 15.0 | B2 | 15.0 |
| M16 | a1 | 6.16 | b1 | 33.23 | 1.02:1 | B3 | 15.0 | B2 | 15.0 |

| Holographic medium | Non-photopolymerizable component | Proportion (% by weight) | Photoinitiator | Proportion (% by weight) | Auxiliaries and additives | Proportion (% by weight) | Catalyst in solution | Proportion (% by weight) |
|---|---|---|---|---|---|---|---|---|
| M1 | D3 | 15.0 | C3 | 4.59 | E2 | 0.30 | E1 | 0.010 |
| M2 | D7 | 15.0 | C3 | 4.59 | E2 | 0.30 | E1 | 0.010 |

TABLE 3-continued

Holographic media which were tested with regard to their performance Δn

| | | | | | | | | |
|---|---|---|---|---|---|---|---|---|
| M3  | D8  | 15.0 | C3 | 4.59 | E2 | 0.30 | E1 | 0.010 |
| M4  | D2  | 15.0 | C3 | 4.59 | E2 | 0.30 | E1 | 0.010 |
| M5  | D2  | 25.0 | C1 | 5.30 | E2 | 0.30 | E1 | 0.010 |
| M6  | D1  | 25.0 | C1 | 5.30 | E2 | 0.30 | E1 | 0.010 |
| M7  | D2  | 15.0 | C3 | 4.59 | E2 | 0.30 | E1 | 0.010 |
| M8  | D6  | 15.0 | C3 | 4.59 | E2 | 0.30 | E1 | 0.010 |
| M9  | D10 | 15.0 | C3 | 4.59 | E2 | 0.30 | E1 | 0.010 |
| M10 | D1  | 25.0 | C1 | 5.15 | E2 | 0.30 | E1 | 0.100 |
| M11 | D1  | 25.0 | C2 | 5.40 | E2 | 0.30 | E1 | 0.100 |
| M12 | D1  | 15.0 | C3 | 4.59 | E2 | 0.30 | E1 | 0.010 |
| M13 | D9  | 25.0 | C2 | 5.40 | E2 | 0.30 | E1 | 0.050 |
| M14 | D4  | 25.0 | C2 | 5.40 | E2 | 0.30 | E1 | 0.050 |
| M15 | D5  | 25.0 | C2 | 5.40 | E2 | 0.30 | E1 | 0.050 |
| M16 | D1  | 25.0 | C1 | 5.30 | E2 | 0.30 | E1 | 0.010 |

Production of Holographic Media in a Glass Structure

For the production of the holographic media, the writing monomers (component B), the stabilizers (component E) (which may already have been dissolved beforehand in the component C) and optionally the auxiliaries and additives (component E) are dissolved in the isocyanate-reactive component (component b), optionally at 60° C., 10 or 20 μm glass beads (for example from Whitehouse Scientific Ltd, Waverton, Chester, CH3 7PB, United Kingdom) are then added and thoroughly mixed. Thereafter, the photoinitiator or photoinitiators (together with component C), in pure form or in dilute solution in N-ethyl-pyrrolidone (part of component C), is or are weighed in the dark or with suitable illumination and mixing is effected again for 1 minute. Optionally, heating is effected in a drying oven to 60° C. for not more than 10 minutes. Thereafter, the isocyanate component (component a) is added and mixing is effected again for 1 minute. Subsequently, a solution of the catalyst (component E1) is added and mixing is effected again for 1 minute. The mixture obtained is devolatilized with stirring at <1 mbar for not more than 30 seconds and is then distributed on 50×75 mm glass plates and these are each covered with a further glass plate. The curing of the PU formulation takes place under 15 kg weights over several hours (usually overnight). In some cases, the media are postcured in light-tight packaging for a further 2 hours at 60° C. The thickness d of the photopolymer layer is obtained as 20 μm from the diameter of the glass spheres used. Since different formulations with different starting viscosity and different curing rate of the matrix do not always lead to the same layer thicknesses d of the photopolymer layer, d is determined separately on the basis of the characteristics of the recorded holograms for each sample. The media of the comparative media produced in the laboratory (see Table 4) were produced analogously to this method.

The following TGA 95: measured values were determined for the writing monomers B) according to the formula IV described non-photopolymerizable components D):

TABLE 4

List of components B and D which were tested with regard to TGA 95

| Component | Designation | TGA 95 in ° C. |
|---|---|---|
| B1 | Phosphorothioyltris(oxy-4,1-phenyleneiminocarbonyloxyethane-2,1-diyl) triacrylate | 177.2 |
| B2 | 2-({[3-(Methylsulphanyl)phenyl]carbamoyl}oxy)ethyl prop-2-enoate | 190.3 |
| B3 | Mixture of (4-methylbenzene-1,3-diyl)bis[carbamoyloxy-3-(biphenyl-2-yloxy)propane-2,1-diyl] bisacrylate and (4-methylbenzene-1,3-diyl)bis[carbamoyloxy-3-(biphenyl-2-yloxy)propane-1,2-diyl] bisacrylate and analogous isomers | 239.5 |
| D1 | Bis(2,2,3,3,4,4,5,5,6,6,7,7-dodecafluoroheptyl)-(2,2,4-trimethylhexane-1,6-diyl) biscarbamate | 189.5 |
| D2 | 2,2,3,3,4,4,5,5,6,6,7,7,8,8,9,9-Hexadecafluorononyl butylcarbamate | 111.8 |
| D3 | 2,2,2-Trifluoroethyl hexylcarbamate | 72.5 |
| D4 | Bis(1,1,1,3,3,3-hexafluoropropan-2-yl)-(2,2,4-trimethylhexane-1,6-diyl) biscarbamate | 139.1 |
| D5 | 2,2,3,3,4,4,5,5,6,6,7,7-Dodecafluoroheptyl butylcarbamate | 112.6 |
| D6 | 2,2,3,3,4,4,5,5,6,6,7,7-Dodecafluoroheptyl hexylcarbamate | 117.6 |
| D7 | 2,2,3,3,4,4,5,5,6,6,7,7-Dodecafluoroheptyl propan-2-ylcarbamate | 93.3 |
| D8 | 2,2,3,3,4,4,4-Heptafluorobutyl hexylcarbamate | 82.3 |
| D9 | 2,2,3,3,4,4,5,5,6,6,7,7,8,8,9,9-Hexadecafluorononyl hexylcarbamate | 125.9 |
| D10 | 2,2,3,3,4,4,5,5,6,6,7,7,8,8,9,9-Hexadecafluorononyl cyclohexylcarbamate | 130.8 |

Results of the Holographic Property Δn

The following measured values of the holographic media described in Table 3 are shown in Table 5:

TABLE 5

Holographic measured results Δn as a function of various compositions and drying conditions

| Holographic medium | Example type | Drying (time min/ temperature ° C.) | Dry layer thickness (μm) | Δn (633 nm) | E (mJ/cm²) | Δn (532 nm) | E (mJ/cm²) |
|---|---|---|---|---|---|---|---|
| M1 | Comparative Example 1 | 4.5/80 | 12-14 | 0.012 | 9-36 | | |
| M2 | Comparative Example 2 | 4.5/80 | 15-17 | 0.011 | 9-36 | | |
| M3 | Comparative Example 3 | 4.5/80 | 15-16 | 0.011 | 9-36 | | |
| M4 | Comparative Example 4 | 4.5/100 | 16-18 | 0.010 | 9-36 | | |
| M5 | Example 1 | 4.5/80 | 12-14 | 0.037 | 9-36 | 0.034 | 16-128 |
| M6 | Example 2 | 4.5/80 | 15-16 | 0.034 | 9-36 | 0.032 | 16-128 |
| M7 | Example 3 | 4.5/80 | 15-16 | 0.038 | 9-36 | | |
| M8 | Example 4 | 4.5/80 | 16-17 | 0.027 | 9-36 | | |
| M9 | Example 5 | 4.5/80 | 16-17 | 0.029 | 9-36 | | |
| M10 | Example 6 | 4.5/80 | 11-12 | | | 0.031 | 16-128 |
| M11 | Example 7 | 4.5/80 | 15-17 | 0.036 | 9-36 | | |
| M12 | Example 8 | 4.5/80 | 11-13 | 0.031 | 9-36 | | |
| M13 | Example 9 | 4.5/80 | 15-17 | 0.037 | 9-36 | 0.035 | 16-128 |
| M14 | Example 10 | 4.5/80 | 15-17 | 0.028 | 9-36 | 0.033 | 16-128 |
| M15 | Example 11 | 4.5/80 | 15-17 | 0.029 | 9-36 | 0.030 | 16-128 |
| M16 | Example 12 | 4.5/80 | 12-13 | 0.037 | 9-36 | 0.033 | 16-128 |

The choice of suitable photopolymer formulations is made on the one hand by a comparison of the measured Δn values in the film structure. Examples M5 to M16 are convincing here.

Table 6 shows the direct comparison of the media produced in the laboratory with the photopolymer formulations cured in the open

TABLE 6

Comparison of the holographic measured results Δn of the photopolymer in the film structure with photopolymers which were prepared in the laboratory

| Holographic medium | Example type | Drying (time min/ temperature ° C.) | Dry layer thickness (μm) | Δn (633 nm) of film structure | E (mJ/cm²) | Δn (633 nm) of laboratory medium | E (mJ/cm²) |
|---|---|---|---|---|---|---|---|
| M1 | Comparative example 1 | 4.5/80 | 12-14 | 0.012 | 9-36 | 0.024 | 9-36 |
| M2 | Comparative example 2 | 4.5/80 | 15-17 | 0.011 | 9-36 | 0.035 | 9-36 |
| M3 | Comparative example 3 | 4.5/80 | 15-16 | 0.011 | 9-36 | 0.033 | 9-36 |
| M4 | Comparative example 4 | 4.5/100 | 16-18 | 0.010 | 9-36 | 0.039 | 9-36 |
| M5 | Example 1 | 4.5/80 | 12-14 | 0.037 | 9-36 | 0.039 | 9-36 |
| M7 | Example 3 | 4.5/80 | 15-16 | 0.038 | 9-36 | 0.039 | 9-36 |
| M8 | Example 4 | 4.5/80 | 16-17 | 0.027 | 9-36 | 0.025 | 9-36 |
| M9 | Example 5 | 4.5/80 | 16-17 | 0.029 | 9-36 | 0.030 | 9-36 |
| M12 | Example 8 | 4.5/80 | 11-13 | 0.031 | 9-36 | 0.037 | 9-36 |

The comparison from Table 6 shows that the holographic property Δn in the film structure of experiments M1 to M4 do not agree with the results from the photopolymer produced in the laboratory. Examples M5-M12 on the other hand show virtually comparable holographic properties.

Thus, the photopolymer formulations of Examples M5 to M16 can be identified as suitable formulations for the industrial production of holographic films having very good holographic properties.

The invention claimed is:
1. A process for producing holographic media comprising: determining the TGA 95 of compounds useful as components for a photopolymer formulation,
 i) providing the photopolymer formulation comprising:
  A) matrix polymers,
  B) writing monomers,
  C) a photoinitiator system,
  D) optionally a non-photopolymerizable component, and
  E) optionally catalysts, free radical stabilizers, solvents, additives and other auxiliaries and/or additives;
 ii) applying the photopolymer formulation as a layer to a substrate film; and
 iii) drying the photopolymer formulation on the substrate film at a temperature (T) of between 60 to 120° C.;
wherein the components chosen for the photopolymer formulation are only compounds having a TGA 95 value greater than 100° C. and are at least 30° C. above the temperature (T), and wherein the TGA 95 values of the individual components are determined by weighing an amount of about 10 mg of the sample of the respective component into a small aluminium pan having a volume of 70 μl, introducing the small aluminium pan an oven of a thermobalance, and measuring the loss of mass of the sample in the open small aluminium pan at a constant oven heating rate of 20 K/min, the start temperature of the oven being 30° C. and the end temperature 600° C., the oven being flushed with a 200 ml/min nitrogen stream during the determination and the temperature at which a loss of mass of the sample of 5% by weight, based on the originally weighed in amount of the sample, has occurred being determined as the TGA 95 value of the respective component.

2. The process according to claim 1, wherein the photopolymer formulation is dried at a temperature of between 70 to 100° C.

3. The process according to claim 1, wherein the matrix polymers comprise polyurethanes.

4. The process according to claim 3, wherein the polyurethanes are obtained by reacting an isocyanate component a) and an isocyanate-reactive component b).

5. The process according to claim 1, wherein the writing monomers comprise acrylates and/or methacrylates.

6. The process according to claim 1, wherein the writing monomers comprise a combination of a monofunctional and a polyfunctional writing monomer.

7. The process according to claim 6, wherein the monofunctional writing monomer has the formula (II)

(II)

wherein
R1, R2, R3, R4, and R5, in each case independently of one another, represent a hydrogen or halogen atom or a C1-C6-alkyl, trifluoromethyl, C1-C6-alkylthio, C1-C6-alkylseleno, C1-C6-alkyltelluro or nitro group, with the proviso that at least one substituent of the group R1, R2, R3, R4, R5 is not hydrogen,
R6, R7, in each case independently of one another, represent hydrogen or a C1-C6-alkyl group, and
A represents a saturated or unsaturated or linear or branched C1-C6-alkyl radical or a polyethylene oxide radical or a polypropylene oxide radical having in each case 2-6 repeating units in the polymer chain.

8. The process according to claim 7, wherein the monofunctional writing monomer has a glass transition temperature of less than 0° C. and a refractive index of greater than 1.50 at 405 nm.

9. The process according to claim 1, wherein the photopolymer formulation comprises urethanes as a plasticizer.

10. The process according to claim 9, wherein the urethanes are substituted by at least one fluorine atom.

11. The process according to claim 10, wherein the urethanes have the formula (IV).

(IV)

wherein
n is from 1 to 8 and
$R^{10}$, $R^{11}$, $R^{12}$, independently of one another, represent hydrogen or linear, branched, cyclic or heterocyclic organic radicals which are unsubstituted or optionally also substituted by heteroatoms.

12. The process according to claim 11, wherein at least one of the radicals R10, R11, R12 are substituted by at least one fluorine atom.

13. The process according to claim 11, wherein R10 represents an organic radical having at least one fluorine atom.

14. The process according to claim 1, wherein the photoinitiator system comprises an anionic, cationic or neutral dye and a coinitiator.

15. The process according to claim 1, wherein the photopolymer formulation is applied as a film to a substrate film and the film is covered by a protective film.

* * * * *